United States Patent [19]

Cimber

[11] Patent Number: 4,612,924
[45] Date of Patent: Sep. 23, 1986

[54] INTRAUTERINE CONTRACEPTIVE DEVICE

[76] Inventor: Hugo Cimber, Neufeldstrasse 134, 3012 Berne, Canton of Berne, Switzerland

[21] Appl. No.: 396,656

[22] Filed: Jul. 9, 1982

[30] Foreign Application Priority Data

Jul. 14, 1981 [CH] Switzerland .................. 4615/81

[51] Int. Cl.⁴ .................................. A61F 5/47
[52] U.S. Cl. ........................... 128/130; 128/129
[58] Field of Search ................ 128/127, 129, 130

[56] References Cited

U.S. PATENT DOCUMENTS

| | | | |
|---|---|---|---|
| 3,405,711 | 10/1968 | Bakunin | 128/130 |
| 3,817,248 | 6/1974 | Buckles et al. | 128/260 |
| 3,918,443 | 11/1975 | Vennard et al. | 128/130 |
| 3,933,153 | 1/1976 | Csatary et al. | 128/129 |
| 4,326,511 | 4/1982 | Zimerman | 128/130 |
| 4,353,363 | 10/1982 | Quesada | 128/130 |

FOREIGN PATENT DOCUMENTS 2537620  2/1977  Fed. Rep. of Germany ...... 128/129

Primary Examiner—Paul J. Hirsch
Attorney, Agent, or Firm—Ronald G. Goebel

[57] ABSTRACT

A support body to be inserted in the uterus is connected to inflatable occluding members intended and adapted solely to seal the mouths of the Fallopian tubes when inflated. Because there is no pressure contact between the device and the walls of the uterus proper, there is no impediment to the flow of menstrual blood nor any risk of harmful effects caused by pressure. The support body comprises a central piece through which an inflation medium can be introduced into the occluding members, which are disposed at the ends of two branches projecting laterally from the central piece. Thus, the device is easy to position accurately within the uterus. The support body is stiff but resiliently deformable and of stable shape.

3 Claims, 5 Drawing Figures

INTRAUTERINE CONTRACEPTIVE DEVICE

This invention relates to contraceptive devices, and more particularly to an intrauterine contraceptive device of the type having a support body intended to be inserted into the uterus, connected to inflatable portions intended to be positioned in or near the mouths of the Fallopian tubes opening into the uterus.

Besides the conventional intrauterine contraceptive devices (IUDs) which usually take the form of rigid one-piece or multipart bodies and are therefore troublesome to insert and remove, IUDs having a body inflatable by means of a feed tube have been proposed. This body, viewed in plan, takes the form of a triangular bag or of a torus having a closing diaphragm. When inflated, it presses against at least parts of the uterine wall and prevents conception to a certain extent by partially filling the uterus.

One drawback of these prior art devices is that they do not provide the desired degree of contraceptive efficacy; moreover, because the uterus is filled at least partially, menstrual blood cannot flow out properly. A further drawback is that the constant pressure of the inflated body upon the uterine mucous membrane results in a risk of pressure-caused necrosis, or gangrene.

IUDs have already been proposed which comprise portions intended to be situated in or near the mouths of the Fallopian tubes, either for the purpose of positioning and retaining the devices in the uterus (U.S. Pat. No. 3,405,711) or of making contact with the walls of the uterine cavity by adapting to its size and shape through inflation (U.S. Pat. No. 3,918,443). However, these devices are neither designed to seal off the mouths of the Fallopian tubes, nor are they capable of doing so, and both of them contact or exert pressure upon the walls of the uterus.

It is an object of this invention to provide an improved intrauterine contraceptive device which not only prevents undesired pregnancy more effectively than prior art devices but also avoids contact of any sort with the walls of the uterus itself.

A further object of this invention is to provide an intrauterine contraceptive device which is designed in such a way as to facilitate greatly its proper positioning as compared with prior art devices.

To this end, in the intrauterine contraceptive device according to the present invention, of the type initially mentioned, the support body is hollow, is made of stiff but resiliently deformable material which retains its shape, and comprises two branches projecting laterally from a central connection piece, an inflatable portion taking the form of a spherical occluding member being disposed at the free end of each branch, whereby solely the mouths of the Fallopian tubes are reversibly sealed by the occluding members when inflated.

Two preferred embodiment of the invention will now be described in detail with reference to the accompanying drawings, in which.

Figure 1:
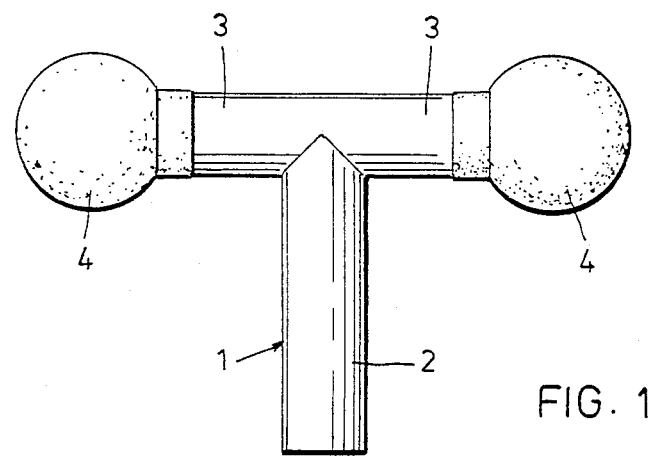
FIGS. 1 and 2 are perspective views of the two embodiments.
Figure 5:
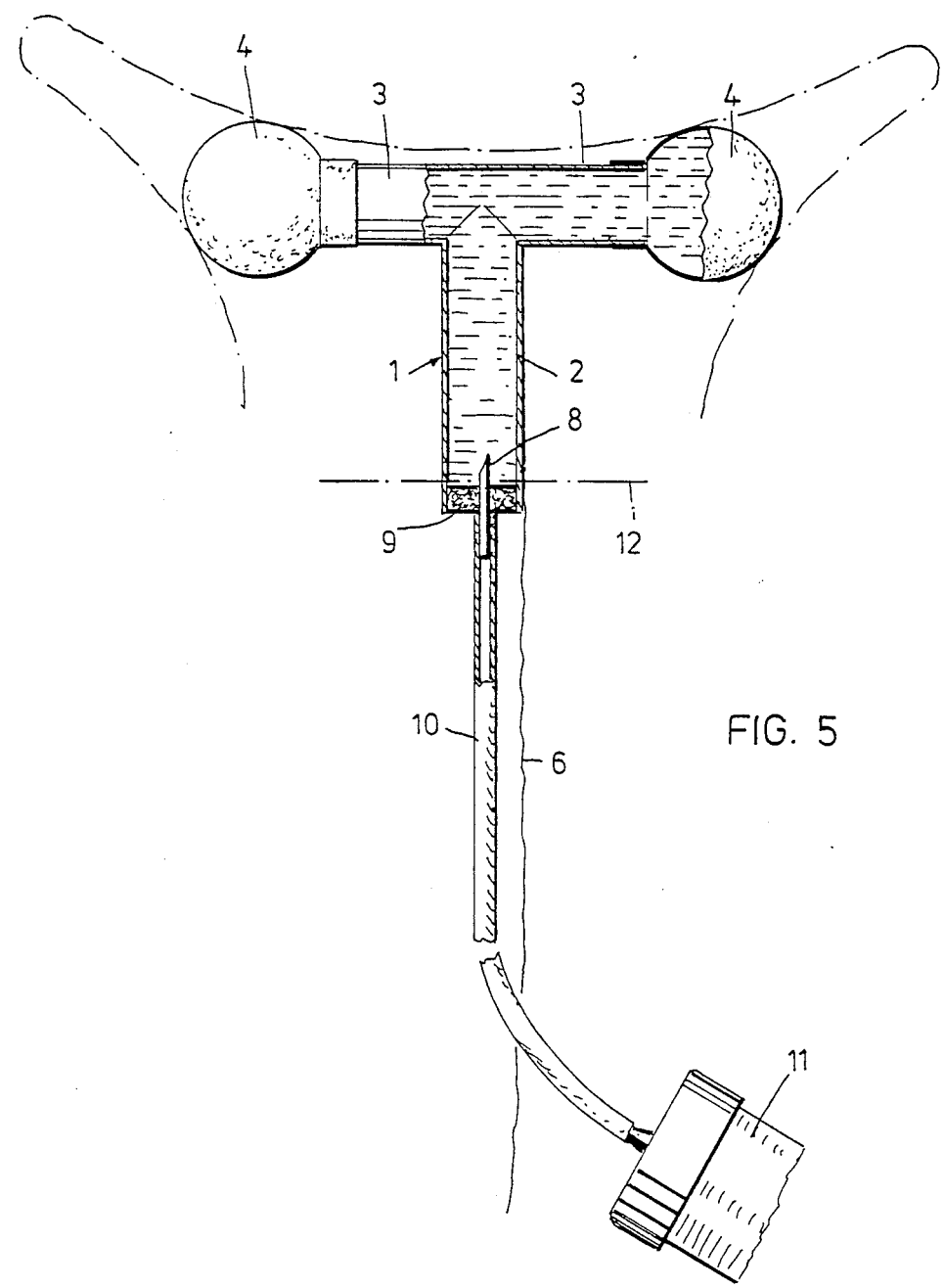
FIG. 5 is a perspective view, partially cut away and in section, showing the device in operative position with a syringe, a catheter, and a needle inserted in the device.

In a first embodiment, illustrated in FIG. 1, the IUD comprises a support body 1 consisting of a stiff but resilient tube of stable shape made of silicone rubber. Support body 1 includes a central connection piece 2 and two branches 3 projecting from piece 2 at right angles on opposite sides, so that support body 1, in the state shown in FIGS. 1 and 5, is substantially T-shaped.

Figure 4:
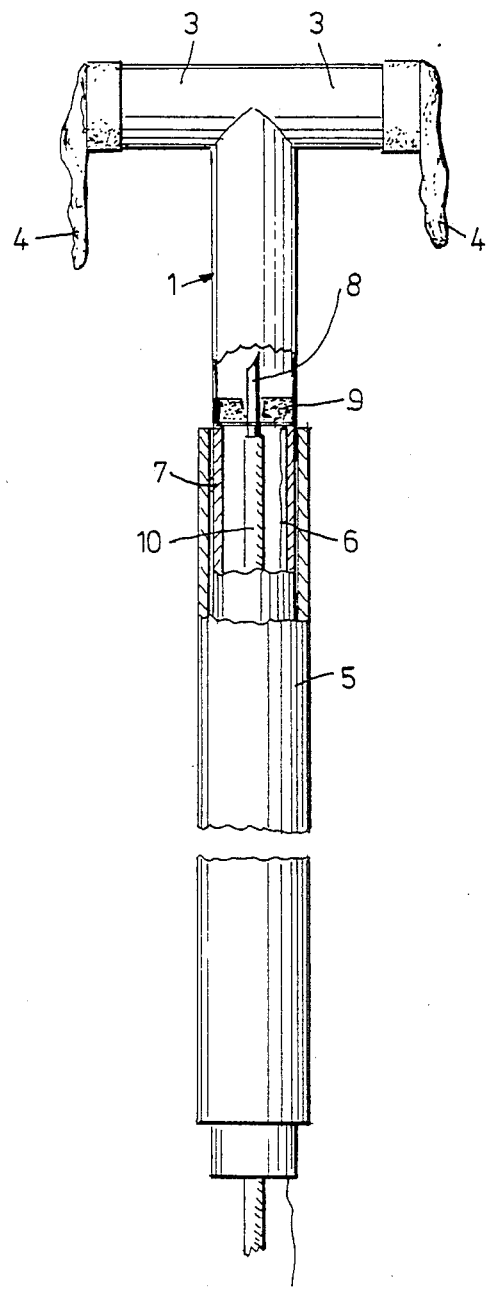
FIG. 4 is a perspective view, partially cut away and in section, of the exterior tube containing an interior tube with the ejected device.

Vulcanized onto the end of each branch 3 is a balloon-like occluding member 4 of thin silicone rubber film, so that when a pressure medium is introduced through connection piece 2, each of the two occluding members 4 can be inflated into a firm balloon, while in the absence of any internal pressure they hang limply at the ends of the two branches 3 (cf. FIG. 4).

Figure 2:
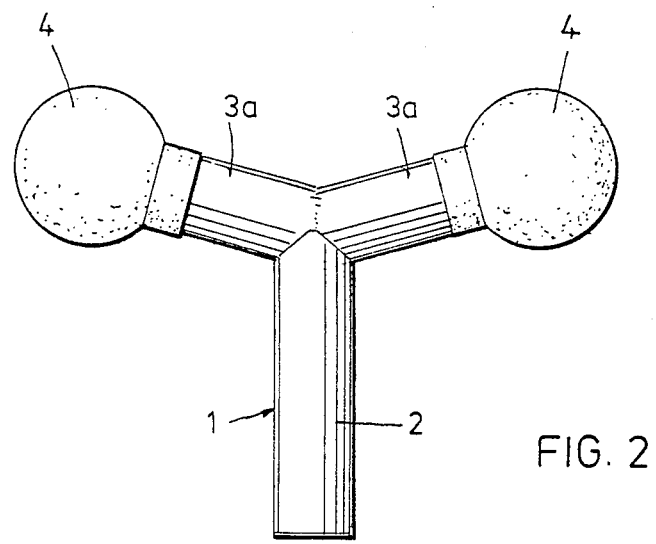

The second embodiment, illustrated in FIG. 2, differs from the first one in that branches 3a are joined to central connection piece 2 at an angle rather than perpendicularly.

Connection piece a may also be cooperplated in order to achieve a dual effect, given the known contraceptive properties of copper.

Figure 3:
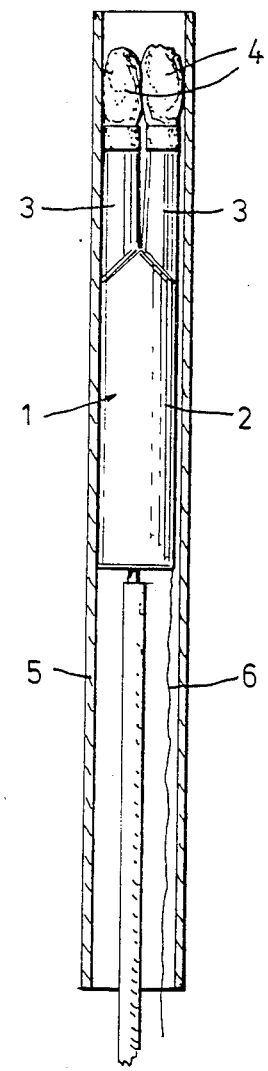
FIG. 3 is a section through an exterior tube containing the device in collapsed form.

FIG. 3 shows an embodiment of the invention according to FIG. 1 or FIG. 2 in an inoperative position in which support body 1 has been drawn into an exterior tube 5, e.g., by means of a thread 6. Branches 3 lie substantially parallel to one another, as well as to connection piece 2, within tube 5.

For the purpose of inserting support body 1 into the uterus, an interior tube 7 is introduced into exterior tube 5 in such a way as to rest against the underside of connection piece 2, as is apparent from FIG. 4. Preferably before the insertion operation, a hypodermic-type needle 8 is stuck through a diaphragm 9 which closes connection piece 2 at the bottom. Needle 8 is connected via a catheter 10 to a pressure-medium source, e.g., a syringe 11.

As soon as support body 1 has been pushed forward into the position shown in FIG. 4 and is inside the uterus, branches 3 or 3a swing into the position illustrated in FIGS. 1 or 2 owing to their inherent resiliency. A pressure medium, e.g., water, is then forced into support body 1 by means of syring 11, causing occluding members 4 to swell like ballons and to lie against the mouths of the Fallopian tubes where they open into the uterus, thus forming a tight seal.

When a liquid is used as the pressure medium, it has proved advantageous to color it in order to be able to detect any leaks immediately.

Because occluding members 4 come in contact with the uterine wall only in the area of the mouths of the Fallopian tubes, indicated diagrammatically in dot-dash lines in FIG. 5, there is no obstacle to the flow of menstrual blood and no danger of any pressure-caused necrosis.

What is more, owing to the relative positions of branches 3 or 3a as established through introduction of the pressure medium, support body 1 can be inserted into the uterus in such a way that is becomes much easier to locate the correct seating points of occluding members 4, i.e., balloon-like members 4 can easily be positioned at the mouths of the Fallopian tubes with greater reliability than it has been possible to position prior art IUDs.

Fastened to the bottom or free end of central connection piece 2 is, as already mentioned, thread 6, which is also used for pulling connection piece 2 out of the orifice of the uterus far enough so that the part of piece 2 to which diaphragm 9 is attached can be cut off. The cutting plane is indicated by a dot-dash line in FIG. 5 and designated by reference numeral 12. The pressure medium then runs out of support body 1 and occluding members 4, so that the latter collapse, and the whole support body 1 can be removed without difficulty, e.g., by means of forceps.

What is claimed is:

1. An intrauterine contraceptive device comprising a hollow support body of stable shape made of stiff but resiliently deformable material, said support body including a central portion and two branch portions projecting laterally from said central portion, and two inflatable members respectively disposed at the ends of said branch portions remote from said central portion, said inflatable members being inflated by introducing a pressure medium into said central portion of said support body and assuming a spherical shape upon inflation within the uterus and being adapted when in operative position to seal the mouths of the Fallopian tubes without pressure contact between said device and the walls of the uterus proper.

2. The intrauterine contraceptive device of claim 1, further comprising a pierceable diaphragm closing the end of said central portion remote from said branch portions.

3. The device of claim 1 wherein said inflatable members are comprised of silicone rubber.

* * * * *